US012760260B2

(12) United States Patent
Okamoto

(10) Patent No.: US 12,760,260 B2
(45) Date of Patent: Oct. 13, 2026

(54) TRANSFER DEVICE FOR LIVING ORGANISMS

(71) Applicant: TOPPAN INC., Tokyo (JP)

(72) Inventor: Shinichi Okamoto, Tokyo (JP)

(73) Assignee: TOPPAN INC., Tokyo (JP)

( * ) Notice: Subject to any disclaimer, the term of this patent is extended or adjusted under 35 U.S.C. 154(b) by 880 days.

(21) Appl. No.: 17/883,957

(22) Filed: Aug. 9, 2022

(65) Prior Publication Data

US 2022/0380714 A1 Dec. 1, 2022

Related U.S. Application Data

(63) Continuation of application No. PCT/JP2021/005143, filed on Feb. 12, 2021.

(30) Foreign Application Priority Data

Feb. 14, 2020 (JP) ................................ 2020-023725

(51) Int. Cl.
*C12M 1/32* (2006.01)
*A61M 37/00* (2006.01)
*C12M 1/26* (2006.01)

(52) U.S. Cl.
CPC ............ *C12M 33/06* (2013.01); *A61M 37/00* (2013.01); *C12M 33/04* (2013.01)

(58) Field of Classification Search
None
See application file for complete search history.

(56) References Cited

U.S. PATENT DOCUMENTS 5,417,683 A * 5/1995 Shiao ........................ A61F 2/10 606/1
5,846,225 A * 12/1998 Rosengart .............. A61K 48/00 604/115
5,868,758 A 2/1999 Markman
2003/0069543 A1* 4/2003 Carpenter ......... A61M 25/0084 604/190
2007/0010810 A1 1/2007 Kochamba
2007/0106306 A1* 5/2007 Bodduluri .............. A61B 34/70 606/133
2010/0330589 A1 12/2010 Bahrami et al.
2013/0197427 A1 8/2013 Merchant et al.
(Continued)

FOREIGN PATENT DOCUMENTS

JP 2008-029331 A 2/2008
JP 2010-536433 A 12/2010
(Continued)

OTHER PUBLICATIONS

International Searching Authority, “International Search Report,” issued in connection with International Patent Application No. PCT/JP2021/005143, dated Apr. 4, 2021.
(Continued)

*Primary Examiner* — Henry H Nguyen
(74) *Attorney, Agent, or Firm* — Foley & Lardner LLP

(57) ABSTRACT

A transfer device for a living organism for placing an object in a living organism comprises a plurality of movable units. Each movable unit comprises one or more needles extending in a first direction. Each needle has a cylindrical shape capable of storing the object therein. Each movable unit is movable in the first direction.

17 Claims, 12 Drawing Sheets

(56) References Cited

U.S. PATENT DOCUMENTS

| | | | | |
|---|---|---|---|---|
| 2014/0037592 | A1 | 2/2014 | Toyoshima et al. | |
| 2017/0014608 | A1* | 1/2017 | Takada ................. | A61K 9/0014 |
| 2019/0062687 | A1 | 2/2019 | Fukuda et al. | |
| 2019/0223908 | A1* | 7/2019 | Kim ................... | A61B 17/3468 |

FOREIGN PATENT DOCUMENTS

| | | | |
|---|---|---|---|
| WO | WO-2007/042818 | A1 | 4/2007 |
| WO | WO-2012/108069 | A1 | 8/2012 |
| WO | WO-2017/073625 | A1 | 5/2017 |
| WO | WO-2019/064653 | A1 | 4/2019 |

OTHER PUBLICATIONS

International Searching Authority, "Written Opinion," issued in connection with International Patent Application No. PCT/JP2021/005143, dated Apr. 4, 2021.

Extended European Search Report issued in corresponding European Patent Application No. 21754246.3, dated Jul. 20, 2023.

* cited by examiner

TRANSFER DEVICE FOR LIVING ORGANISMS

CROSS-REFERENCE TO RELATED PATENT APPLICATIONS

This application is a continuation application filed under 35 U.S.C. § 111(a) claiming the benefit under 35 U.S.C. §§ 120 and 365(c) of International Patent Application No. PCT/JP2021/005143, filed on Feb. 12, 2021, which in turn claims the benefit of JP 2020-023725, filed Feb. 14, 2020 the disclosures of all which are incorporated herein by reference in its entirety.

TECHNICAL FIELD

The present disclosure relates to a transfer device for a living organism used to transfer an object into a living organism.

BACKGROUND

Techniques for transplanting cell groups into living organisms have been developed. For example, regeneration of hair has been performed by culturing cell groups that contribute to formation of hair follicles, which are organs that produce hair, and transplanting the cell groups into intradermal sites. For good hair regeneration, it is desired that the cell groups transplanted generate hair follicles having a normal tissue structure and good hair formation ability. Therefore, various research and development projects have been performed for methods of producing cell groups that can produce hair follicles (for example, see PTLs 1 to 3).

Further, development of a cell transplantation device, which is a device for transferring the cultured cell group from a culture container to a living organism, is also underway (for example, see PTL 4). The cell transplantation device comprises a needle, which is a cylindrical structure with a needle-like point, and incorporates a cell group from a culture container into the inside of the needle. After the needle punctures a target site of transplantation, such as skin, the cell group is released from the tip of the needle, so that the cell group is placed in the living organism. A cell transplantation device comprising a plurality of needles can collectively transplant a plurality of cell groups, and thus can increase the transplantation efficiency.

[Citation List] [Patent Literature] PTL 1: WO2017/073625; PTL 2: WO2012/108069; PTL 3: JP 2008-29331 A; PTL 4: WO2019/064653.

SUMMARY OF THE INVENTION

Technical Problem

In order to exert the effects of transplantation of cell groups, such as tissue regeneration, it is desired that the survival rate of the cell groups is high, and that the activity of the cell groups is preferably maintained in the living organism. The placement depth of the cell groups in the living organism during transplantation is one of the factors that affect the survival rate and activity of the cell groups. For this reason, it is preferable that the gap between the planned placement depth of the cell groups and the actual placement depth of the cell groups is small.

However, as the number of needles provided in the cell transplantation device is larger, the target site of transplantation receives greater pressing force and tensile force from the cell transplantation device during insertion and withdrawal of the needles. Further, as the number of needles inserted and withdrawn at close range is larger, the part punctured by each needle receives pressing force and tensile force generated by insertion and withdrawal of the surrounding other needles. Since the skin and organs of a living organism have flexibility and elasticity, the above pressing force and tensile force cause expansion and contraction of the target site. As a result, due to the deviation of the puncture depth of the needles from the planned depth, the deviation of the actual placement depth of the cell groups from the planned depth becomes large.

These problems are common not only in cell transplantation devices, but also in devices for supplying objects, such as solid drugs, from the tissue surface of a living organism into the tissue.

An object of the present disclosure is to provide a transfer device for a living organism that can suppress deviation of the placement depth of an object.

Solution to Problem

In an embodiment, a transfer device for a living organism for placing an object in a living organism is provided. The transfer device for a living organism comprises a plurality of movable units. Each movable unit comprises one or more needles extending in a first direction, and each needle has a cylindrical shape capable of storing the object therein. Each movable unit is configured to be movable in the first direction.

DETAILED DESCRIPTION

Figure 1:
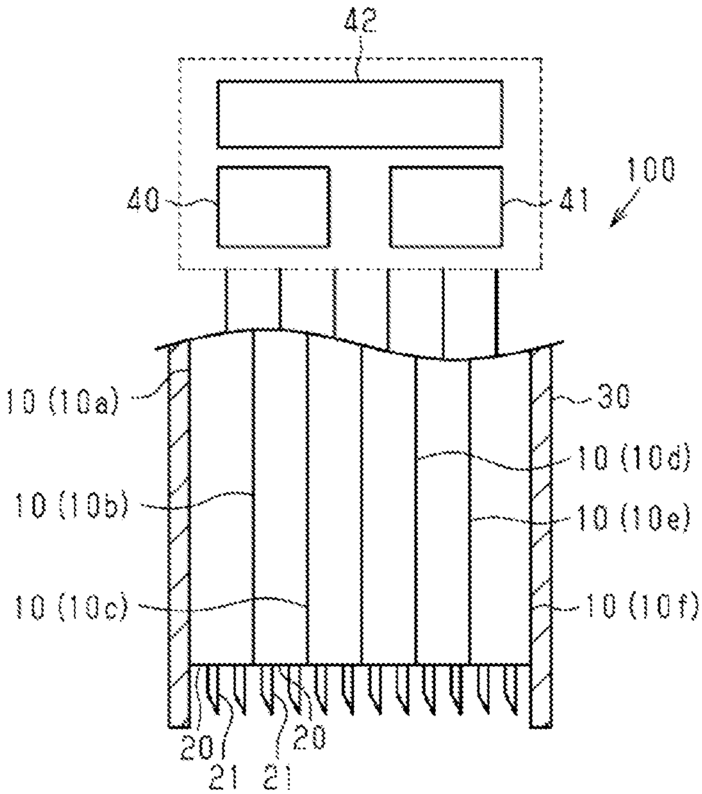
FIG. 1 is a view illustrating a cell transplantation device, which is an example of a transfer device for a living organism in an embodiment of the transfer device for a living organism.

Embodiments of the present invention will be described below with reference to the drawings. In the following description of the drawings to be referred, components or functions identical with or similar to each other are given the same or similar reference signs, unless there is a reason not to. It should be noted that the drawings are only schematically illustrated, and thus the relationship between thickness and two-dimensional size of the components, and the thickness ratio between the layers, are not to scale. Therefore, specific thicknesses and dimensions should be understood in view of the following description. As a matter of course, dimensional relationships or ratios may be different between the drawings.

Further, the embodiments described below are merely examples of configurations for embodying the technical idea of the present invention. The technical idea of the present invention does not limit the materials, shapes, structures, arrangements, and the like of the components to those described below. The technical idea of the present invention can be modified variously within the technical scope defined by the claims. The present invention is not limited to the following embodiments within the scope not departing from the spirit of the present invention. For the sake of clarity, the drawings may be illustrated in an exaggerated manner as appropriate.

In any group of successive numerical value ranges described in the present specification, the upper limit value or lower limit value of one numerical value range may be replaced with the upper limit value or lower limit value of another numerical value range. In the numerical value ranges described in the present specification, the upper limit values or lower limit values of the numerical value ranges may be replaced with values shown in examples. The configuration according to a certain embodiment may be applied to other embodiments.

The embodiments of the present invention are a group of embodiments based on a single unique invention. The aspects of the present invention are those of the group of embodiments based on a single invention. Configurations of the present invention can have aspects of the present disclosure. Features of the present invention can be combined to form the configurations. Therefore, the features of the present invention, the configurations of the present invention, the aspects of the present disclosure, and the embodiments of the present invention can be combined, and the combinations can have a synergistic function and exhibit a synergistic effect.

An embodiment of a transfer device for a living organism will be described with reference to FIGS. 1 to 24. The transfer device for a living organism of the present embodiment is embodied into a cell transplantation device that is used for cell transplantation.

[Transplant]

The cell transplantation device of the present embodiment is used to transplant a transplant into a living organism. The target region of transplantation is at least one of the intradermal and subcutaneous layers, or inside tissues such as organs. The transplant includes a cell group. The cell group to be transplanted will be described.

The cell group to be transplanted includes a plurality of cells. The cell group may be an aggregate of a plurality of cells that are aggregated, or may be an aggregate of a plurality of cells that are joined by intercellular junctions. Alternatively, the cell group may be composed of a plurality of dispersed cells. Further, cells included in the cell group may be undifferentiated cells, or may be cells that have been differentiated. The cell group may also include both undifferentiated cells and differentiated cells. The cell group includes, for example, masses of cells (spheroids), germs, tissues, and organs.

The cell group has an ability to control tissue formation in a living organism when placed in a target region. An example of such a cell group is a cell aggregate containing skin-derived stem cells. The cell group to be transplanted contributes to hair growth and hair restoration, for example, when placed in the intradermal or subcutaneous layer. Such a cell group has an ability to function as a hair follicle organ, an ability to differentiate into a hair follicle organ, an ability to induce or promote formation of a hair follicle organ, or an ability to induce or promote formation of hair in a hair follicle. Further, the cell group may include cells that contribute to control of hair color, such as pigment cells or stem cells that differentiate into pigment cells.

Specifically, an example of the cell group to be transplanted in the present embodiment is a hair follicle germ, which is a primitive hair follicle organ. The hair follicle germ includes mesenchymal cells and epithelial cells. In the hair follicle organ, dermal papilla cells, which are mesenchymal cells, induce differentiation of hair follicle epithelial stem cells to form a hair bulb, and hair matrix cells in the hair bulb repeat division to form a hair. The hair follicle germ is a cell group that differentiates into such hair follicle organs.

The hair follicle germ is formed, for example, by culturing a mixture of mesenchymal cells derived from mesenchymal tissues such as dermal papilla and epithelial cells derived from epithelial tissues located in a bulge region or a hair bulb base under predetermined conditions. It should be noted that the process of forming hair follicle germs is not limited to the above example. In addition, the mesenchymal cells and epithelial cells used for formation of hair follicle germs may also be derived from any tissue. These cells may be derived from a hair follicle organ, may be derived from an organ different from the hair follicle organ, or may be derived from a pluripotent stem cell.

The transplant may include, together with a cell group, a member that assists the transplantation of the cell group.

[Cell Transplantation Device]

As shown in FIG. 1, a cell transplantation device 100 comprises a plurality of movable units 10 and an outer peripheral part 30 surrounding the plurality of movable units 10.

Each movable unit 10 comprises one or more needles 21 and a support part 20 that supports the needles 21. The needle 21 has a cylindrical shape extending along one direction; in other words, it has a hollow needle-like shape. The outer shape of the needle 21 is not particularly limited, as long as its tip part has a shape capable of puncturing a target site of transplantation, such as skin, in a living organism. The tip part of the needle 21 has, for example, a cylindrical shape truncated obliquely relative to the extending direction thereof, and is pointed.

The support part 20 surrounds a portion except for the vicinity of the tip part of the needle 21, and supports the needle 21. In other words, the vicinity of the tip part of the needle 21 protrudes from the tip surface of the support part 20 along the extending direction of the needle 21. For example, the needle 21 is allowed to pass through a hole in the support part 20, thereby assembling the needle 21 in the support part 20. When the movable unit 10 comprises a plurality of needles 21, the support part 20 collectively supports the plurality of needles 21. The plurality of needles 21 are supported by one support part 20, so that the plurality of needles 21 and the support part 20 integrally form the movable unit 10.

The movable unit 10 is configured to be movable along the extending direction of the needle 21. The materials of the needle 21 and support part 20 are not particularly limited, and these may be made of, for example, resin or metal.

The number of movable units 10 provided in the cell transplantation device 100 is not particularly limited, as long as it is 2 or more. The outer peripheral part 30 surrounds the outer side of an assembly of the movable units 10. The arrangement of the plurality of movable units 10 is not particularly limited, and the plurality of movable units 10 may be regularly arranged, for example, in a two-dimensional lattice shape such as square or hexagonal lattices, or concentrically or linearly, or may be irregularly arranged. Moreover, in the adjacent movable units 10, the tip surfaces of the support part 20 may be in contact or separated.

In the plurality of movable units 10, the number and arrangement of needles 21 provided in each movable unit 10 may be the same or different. Further, in a state in which a plurality of movable units 10 are arranged, in other words, in an assembly comprising a plurality of movable units 10, a plurality of needles 21 provided in the cell transplantation device 100 may be arranged regularly or irregularly. FIG. 1 shows an embodiment in which the cell transplantation device 100 comprises six movable units 10, and each movable unit 10 comprises two needles 21. The six movable units 10 are arranged, from the left side of the figure, in the order from a movable unit 10*a*, a movable unit 10*b*, a movable unit 10*c*, a movable unit 10*d*, a movable unit 10*e*, and a movable unit 10*f*. In the assembly comprising six movable units 10, the needles 21 are arranged at predetermined intervals.

In order to increase the transplantation efficiency, the sum of the needles 21 provided in the plurality of movable units 10, i.e., the sum of the needles 21 provided in the cell transplantation device 100, is preferably 5 or more. In the cell transplantation device 100, the needles 21 are preferably arranged at a density of 5 or more per $cm^2$. The number of needles 21 provided in one movable unit 10 is preferably 10 or less.

The cell transplantation device 100 further comprises a driving part 40, a suction pressure part 41, and a control part 42. The driving part 40 moves the plurality of movable units 10 by each movable unit 10 along the extending direction of the needles 21. Specifically, the driving part 40 moves the movable unit 10 with respect to the outer peripheral part 30 between a state in which the tip parts of the needles 21 of the movable unit 10 are located in a space surrounded by the outer peripheral part 30, and a state in which the tip parts of the needles 21 of the movable unit 10 protrude from the space. That is, the driving part 40 moves the movable unit 10 between a position in which the tip parts of the needles 21 do not protrude more than the tip part of the outer peripheral part 30, and a position in which the tip parts of the needles 21 protrude more than the tip part of the outer peripheral part 30.

The driving part 40 includes an electrical component such as a motor, and moves the plurality of movable units 10 independently, namely moves each movable unit 10 separately, depending on the control signal from the control part 42.

The suction pressure part 41 assists incorporation and release of the transplant into and from the needle 21. The suction pressure part 41 applies suction to the inside of the needle 21 to incorporate the transplant into the needle 21, and pressurizes the inside of the needle 21 to release the transplant from the needle 21.

The suction pressure part 41 suctions and pressurizes the needles 21 of each movable unit 10 in response to the control signal from the control part 42. The suction pressure part 41 may perform suction and pressurization of the needles 21 separately for each movable unit 10, or may perform suction and pressurization of the needles 21 provided in the plurality of movable units 10 collectively for the plurality of movable units 10. The suction pressure part 41 includes a mechanism such as syringe or pump that allows suction and pressurization, and is connected to each movable unit 10 so as to enable suction and pressurization within the needles 21.

The control part 42 controls the operation of the movable units 10. Specifically, the control part 42 controls the timing of the movement of each movable unit 10 by the driving part 40. Moreover, the control part 42 controls the timing of suction and pressurization of the needles 21 in each movable unit 10 by the suction pressure part 41, that is, the timing of incorporation and release of the transplant into and from the needles 21. The control part 42 includes a control circuit generating control signals for controlling, and a memory. Specifically, the control part 42 may comprise an application-specific integrated circuit (ASIC) that is dedicated hardware executing at least part of the various types of processing. The control part 42 may be configured as a circuit including one or more dedicated hardware circuits such as an ASIC, microcomputers that are one or more processors that operate according to software that is a computer program, or a combination thereof.

An example of the detailed structure of the needle 21 will be described with reference to FIG. 2. The needle 21 comprises a first tube 22 including the tip part of the needle 21, and a second tube 23 having a larger flow passage cross-sectional area than the first tube 22. The first tube 22 and the second tube 23 each have a cylindrical shape with a certain inner diameter, and extend along the extending direction of the needle 21. The tip part of the first tube 22 forms the tip part of the needle 21 and has an opening 25. The second tube 23 is connected to the base end part of the first tube 22. The internal space of the first tube 22 and the internal space of the second tube 23 communicate with each other and form one flow passage.

The needle 21 comprises a stopper 24 near the place where the flow passage cross-sectional area changes. The stopper 24 crosses the flow passage in the needle 21 in the middle of the flow passage. The stopper 24 allows the passage of a liquid material from the tip side of the needle 21 to the base end side with respect to the stopper 24, and prevents the passage of the transplant.

The stopper 24 has, for example, a plurality of fibers arranged in a mesh shape, and is covered on the base end part of the first tube 22. The base end part of the first tube 22 covered with the stopper 24 is inserted into the tip part of the second tube 23. The number, material, and arrangement of the fibers in the stopper 24 are not particularly limited, as long as the passage of the transplant can be prevented.

Figure 2:
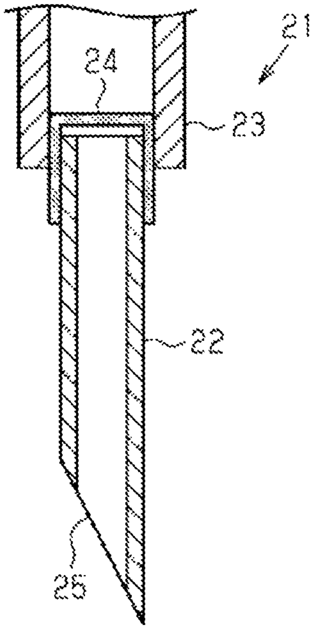
FIG. 2 is a view illustrating an example of the structure of a needle provided in a cell transplantation device of an embodiment.

The needle 21 is not limited to the structure shown in FIG. 2, and may have a cylindrical structure that allows incorporation of the transplant from the opening 25 of the tip part into the needle 21, and accommodation of the transplant inside the needle 21. However, in order to increase the transplantation efficiency, the needle 21 is preferably configured to retain the incorporated transplant near the tip part in the needle 21, like the stopper 24. The needle 21 and the support part 20 may be integrally formed.

[Transplantation Method]

A method for transplanting a transplant using the cell transplantation device 100 will be described.

Figure 3:
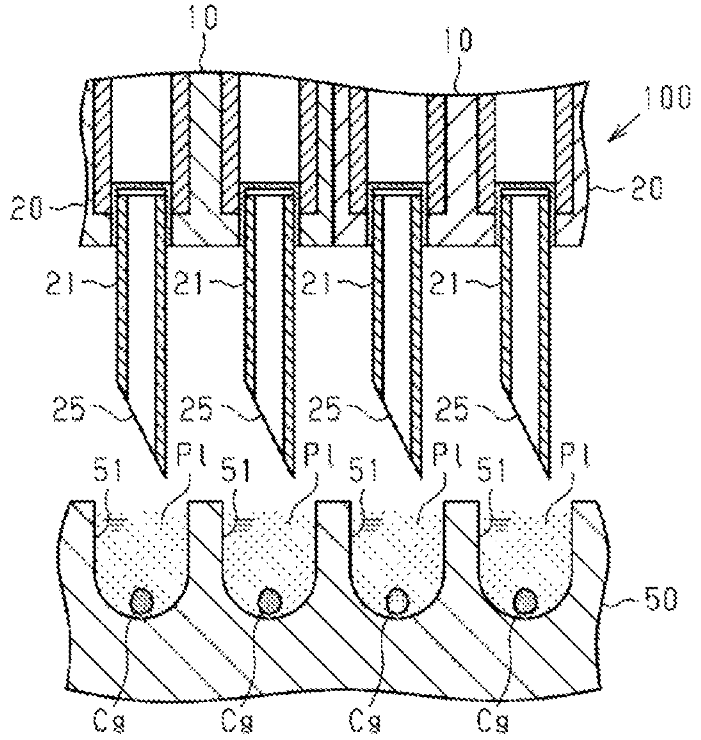
FIG. 3 is a view illustrating an accommodating step of a transplant in a transplantation method using a cell transplantation device of an embodiment.

First, the accommodating step of a transplant will be described. As shown in FIG. 3, transplants Cg are retained in a tray 50, such as a culture container, together with a protective liquid Pl before transplantation. For example, as shown in FIG. 3, the transplants Cg and the protective liquid Pl are placed in recesses 51 of the tray 50. The way of retaining the transplants Cg and the protective liquid Pl in the tray 50 is not limited to the way of retaining the transplants Cg and the protective liquid Pl in the recesses 51. For example, the transplants Cg and the protective liquid Pl may be arranged on the plane of the tray 50. Moreover, the tray 50 may be a container different from the culture container, and the transplants Cg may be transferred from the culture container to the tray 50.

The protective liquid Pl may be any liquid that is unlikely to hinder the viability of cells, and is preferably a liquid that has a small influence on a living organism when injected into the living organism. For example, the protective liquid Pl is physiological saline, a skin-protecting liquid such as Vaseline or lotion, or a mixture of these liquids. The protective liquid Pl may contain additive components such as a nutrient composition. When the tray 50 is a culture container and the transplants Cg are cultured in the tray 50, the protective liquid Pl may be a medium for culturing cells, or may be a liquid exchanged from the medium. The liquid material that contains the transplants Cg and the protective liquid Pl may be a low-viscosity fluid or a high-viscosity fluid.

Figure 4:
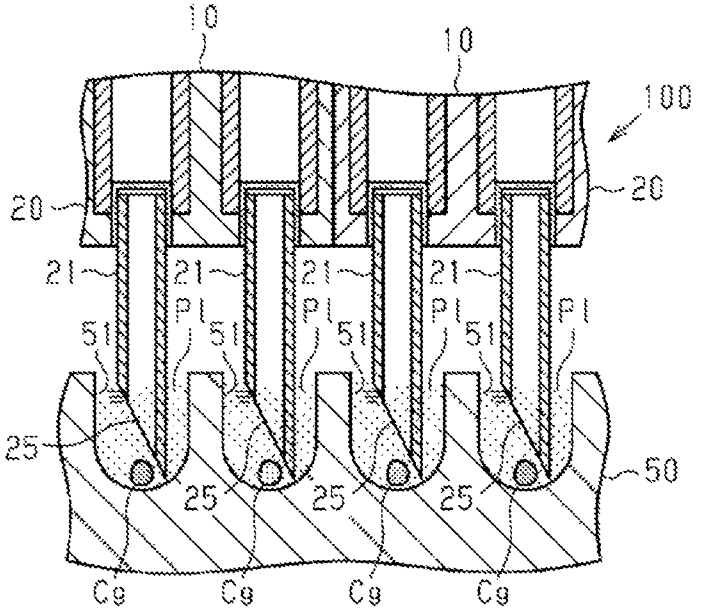
FIG. 4 is a view illustrating an accommodating step of a transplant in a transplantation method using a cell transplantation device of an embodiment.
Figure 5:
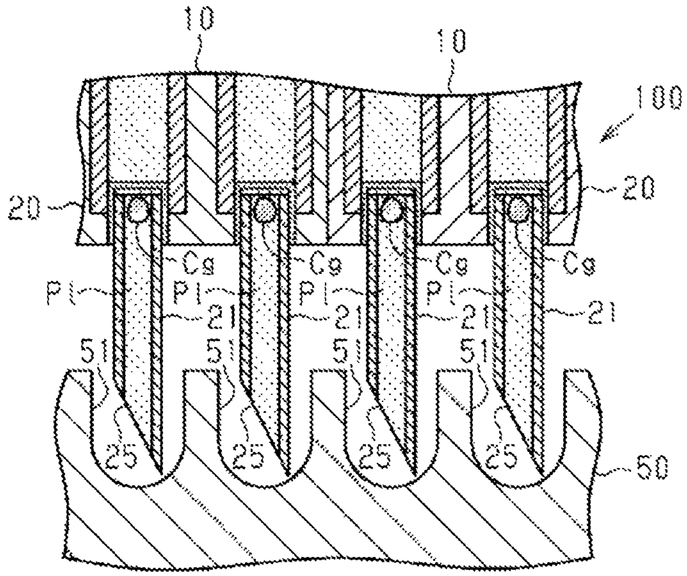
FIG. 5 is a view illustrating an accommodating step of a transplant in a transplantation method using a cell transplantation device of an embodiment.

When the transplants Cg are incorporated, the tip parts of the needles 21 are allowed to face portions of the tray 50 where the transplants Cg are located together with the protective liquid Pl. Then, together with the protective liquid Pl, the transplants Cg are incorporated into the inside of the needles 21 from the openings 25 of the needles 21. For example, the recesses 51 of the tray 50 and the needles 21 are aligned, as shown in FIG. 3, and then the tip parts of the needles 21 are put into the recesses 51, as shown in FIG. 4. Then, by the action of the suction pressure part 41, the transplants Cg, together with the protective liquid Pl, are drawn into the needles 21 from the openings 25, as shown in FIG. 5.

The transplant Cg entering the inside of the needle 21 from the opening 25 moves, together with the flow of the protective liquid Pl, along the flow passage inside the needle 21 toward the stopper 24. To allow the passage of the protective liquid Pl by the stopper 24, the protective liquid Pl flows along the flow of suction in the needle 21 toward the base end side. The stopper 24, however, does not allow the passage of the transplant Cg; thus, the transplant Cg is retained closer to the tip side than to the stopper 24. Thus, the transplant Cg is accommodated in the vicinity of the tip part of the needle 21. The protective liquid Pl is located around the transplant Cg. When the transplant Cg is incorporated, suction is stopped.

The incorporation of the transplants Cg is preferably performed collectively for all of the needles 21 provided in the cell transplantation device 100. That is, the needles 21 are preferably directed to the transplants Cg in the tray 50 at the same time, and the needles 21 are sucked at the same timing, thereby incorporating the transplant Cg into each needle 21. This enhances the efficiency of incorporating the transplants Cg. The transplants Cg may be incorporated in a state in which the tip parts of the needles 21 protrude more than the tip part of the outer peripheral part 30, or in a state in which the tip parts of the needles 21 do not protrude more than the tip part of the outer peripheral part 30. When the tip parts of the needles 21 are aligned, it is easy to collectively incorporate the transplants Cg.

Figure 6:
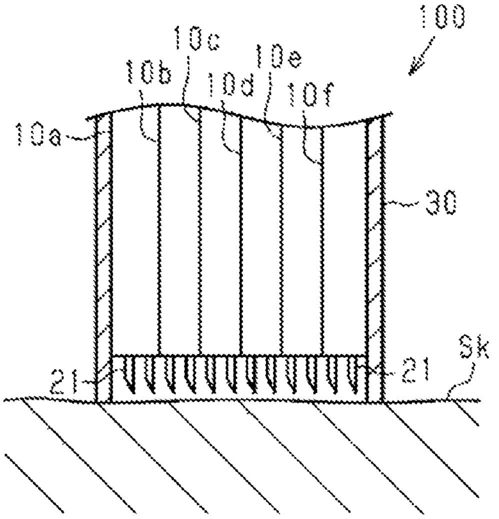
FIG. 6 is a view illustrating a penetration step of needles in a transplantation method using a cell transplantation device of an embodiment.

Subsequently, the penetration step of the needles 21 into a target site of transplantation will be described. As shown in FIG. 6, the position of each movable unit 10 is such that the tip parts of the needles 21 are located in a space surrounded by the outer peripheral part 30, and the cell transplantation device 100 is brought into contact with the target site Sk of transplantation (e.g., skin) in a living organism. That is, the cell transplantation device 100 is brought into contact with the target site Sk in a state in which the tip part of the outer peripheral part 30 protrudes more than the tip parts of all of the needles 21. As a result, the tip part of the outer peripheral part 30 is in contact with the surface of the target site Sk, and each needle 21 does not puncture the target site Sk.

Figure 7:
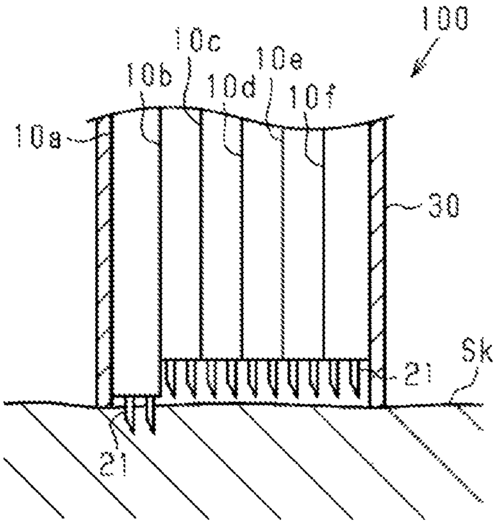
FIG. 7 is a view illustrating a penetration step of needles in a transplantation method using a cell transplantation device of an embodiment.

Next, by the action of the driving part 40, one of the plurality of movable units 10 is moved so that the tip parts of the needles 21 of the movable unit 10 protrude more than the outer peripheral part 30. That is, one movable unit 10 is moved toward the surface of the target site Sk, so that the needles 21 of the movable unit 10 puncture the target site Sk. FIG. 7 shows a state in which, among the six movable units

10, the movable unit 10*a* located on the far left in the figure is moved, so that the needles 21 of the movable unit 10*a* puncture the target site Sk.

Figure 8:
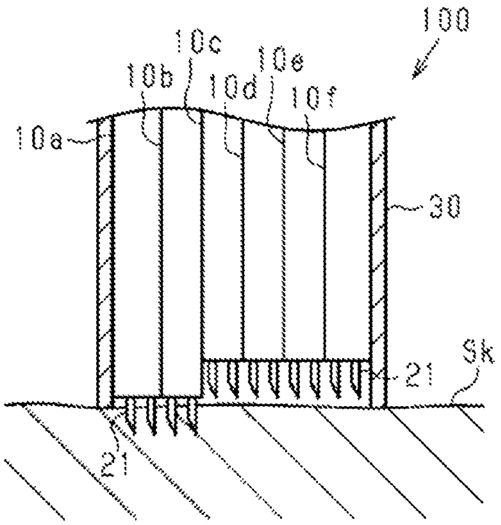
FIG. 8 is a view illustrating a penetration step of needles in a transplantation method using a cell transplantation device of an embodiment.
Figure 9:
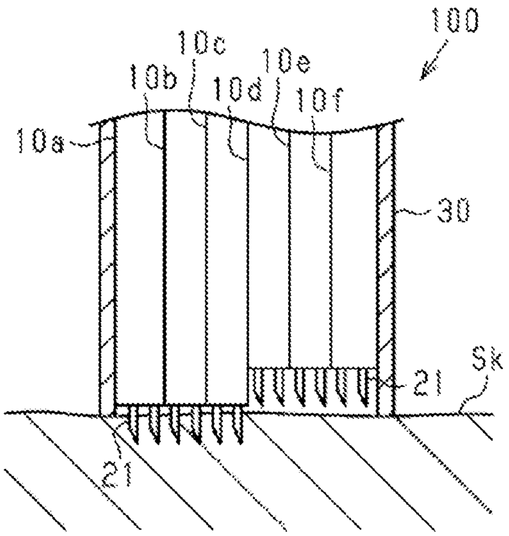
FIG. 9 is a view illustrating a penetration step of needles in a transplantation method using a cell transplantation device of an embodiment.
Figure 10:
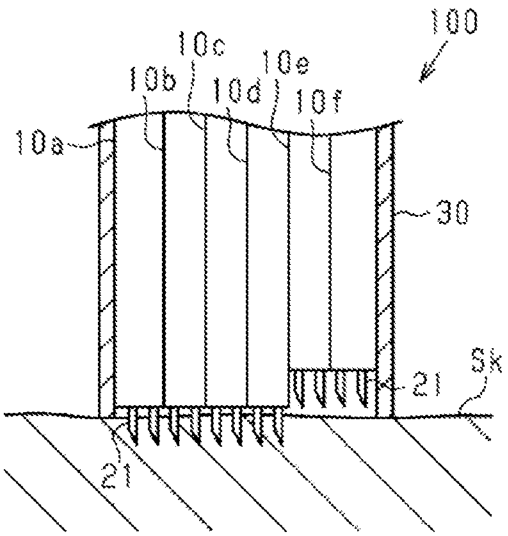
FIG. 10 is a view illustrating a penetration step of needles in a transplantation method using a cell transplantation device of an embodiment.
Figure 11:
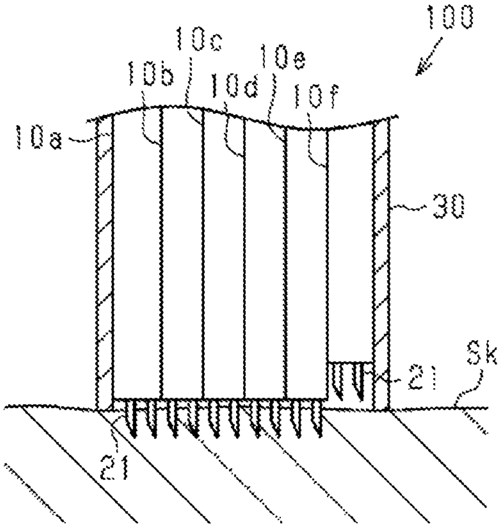
FIG. 11 is a view illustrating a penetration step of needles in a transplantation method using a cell transplantation device of an embodiment.
Figure 12:
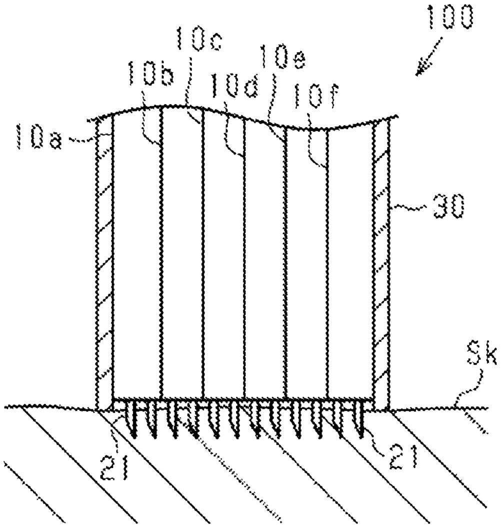
FIG. 12 is a view illustrating a penetration step of needles in a transplantation method using a cell transplantation device of an embodiment.

Similarly, the plurality of movable units 10 are moved one by one, so that the needles 21 puncture the target site Sk in sequence for each movable unit 10. For example, the movable units 10 are moved one by one from left to right in the figure. That is, following the movable unit 10*a*, as shown in FIG. 8, the movable unit 10*b* adjacent to the movable unit 10*a* is moved, so that the needles 21 of the movable unit 10*b* puncture the target site Sk. Subsequently, as shown in FIGS. 9, 10, 11, and 12 in sequence, the movable units 10 are moved in the order from the movable unit 10*c*, the movable unit 10*d*, the movable unit 10*e*, and the movable unit 10*f*, so that the needles 21 of each movable unit 10 puncture the target site Sk. As shown in FIG. 12, when the last movable unit 10*f* is moved, so that the needles 21 of the movable unit 10*f* puncture the target site Sk, the tip parts of the needles 21 of all of the movable units 10 protrude from the tip part of the outer peripheral part 30, and all of the needles 21 of the cell transplantation device 100 puncture the target site Sk.

Thus, the length of each needle 21 puncturing the target site Sk is defined as the length of a portion of each needle 21 protruding from the tip surface of the outer peripheral part 30 based on the tip surface.

Figure 13:
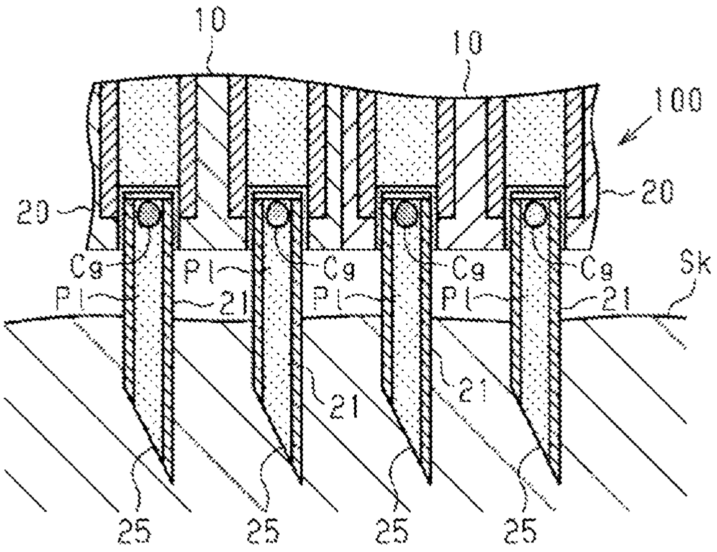
FIG. 13 is a view illustrating a placement step of a transplant in a transplantation method using a cell transplantation device of an embodiment.
Figure 14:
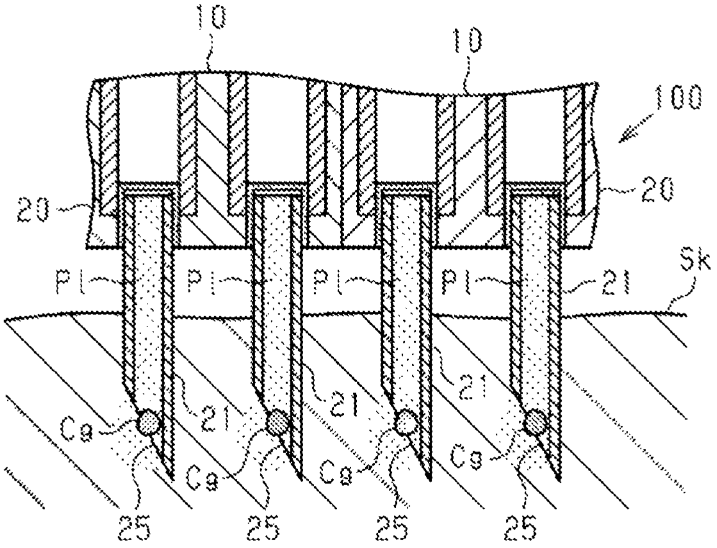
FIG. 14 is a view illustrating a placement step of a transplant in a transplantation method using a cell transplantation device of an embodiment.

When all of the needles 21 of the cell transplantation device 100 puncture the target site Sk, the placement step of the transplants Cg is performed. This placement step will be described. As shown in FIG. 13, while the needles 21 accommodating the transplants Cg puncture the target site Sk, the inside of each needle 21 is pressurized by the action of the suction pressure part 41. As a result, as shown in FIG. 14, the transplants Cg accommodated inside the needles 21 are pushed out together with the protective liquid Pl, and discharged from the opening 25. In this manner, the transplants Cg are placed in the target region of transplantation inside the target site Sk.

The release of the transplants Cg from the needles 21 is preferably performed collectively for all of the needles 21 provided in the cell transplantation device 100. That is, it is preferable that the needles 21 are each pressurized at the same timing to thereby release the transplant Cg from each needle 21. This can enhance the efficiency of placing the transplants Cg in the target region of transplantation.

Figure 15:
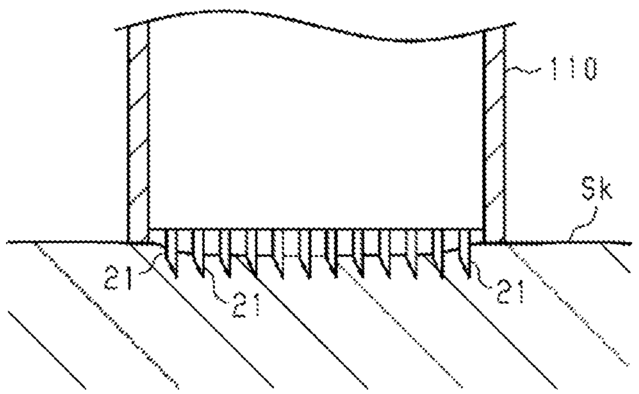
FIG. 15 is a view illustrating a penetration step of needles in a transplantation method using a conventional cell transplantation device.

The action of the cell transplantation device 100 of the present embodiment will be described by comparison between the penetration step and placement step by a conventional cell transplantation device. As shown in FIG. 15, a conventional cell transplantation device 110 does not have movable units that are each independently moved, and all needles 21 puncture the target site Sk at the same time. As a result, the load applied on the target site Sk at one time from the cell transplantation device 110 increases. Further, since many needles 21 puncture the target site Sk at close range, the part punctured by each needle 21 receives tensile force due to the puncture of other surrounding needles 21 from the surrounding area. As a result, the target site Sk tends to be stretched and depressed. Accordingly, the puncture depth of the needles 21 tends to deviate from the planned depth.

Since the target site Sk, which is a living organism, is not stretched uniformly, the degree of depression in the target site Sk varies depending on the puncture position of the needle 21. Thus, since the deviation of the puncture depth of the needle 21 is different for each needle 21, it is difficult for the conventional cell transplantation device 110 to correct the puncture depth of the needle 21. If the puncture depth of the needle 21 is deviated, the placement depth of the transplant Cg released from the tip part of the needle 21 is also deviated from the planned depth.

In contrast, in the cell transplantation device 100 of the present embodiment, a plurality of needles 21 are divided into a plurality of movable units 10, and the needles 21 of the plurality of movable units 10 puncture the target site Sk at different timings. Therefore, compared with the conventional one, the number of needles 21 puncturing the target site Sk at one time is reduced. As a result, the load applied to the target site Sk at one time from the cell transplantation device 100 decreases, and the tensile force received by the part punctured by each the needle 21 from the surrounding area also decreases. Therefore, since depression of the target site Sk is suppressed, the puncture depth of the needle 21 is suppressed from deviating from the planned depth. That is, the placement depth of the transplant Cg is suppressed from deviating from the planned depth. Also, the deformation of the target site Sk is suppressed, which also suppresses the deviation of the placement position of the transplant Cg in the direction along the surface of the target site Sk.

Since it is possible to prevent variations in the puncture depth of the needle 21 among the plurality of needles 21, when trying to place the transplants Cg at the same depth by using the plurality of needles 21, it is also possible to prevent variations in the placement depth of the plurality of transplants Cg.

Figure 16:
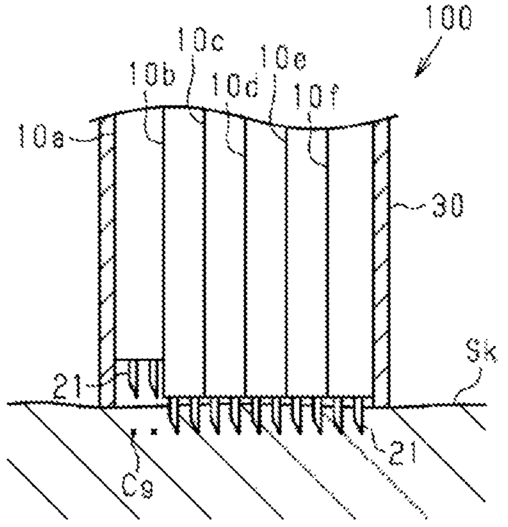
FIG. 16 is a view illustrating a withdrawal step of needles in a transplantation method using a cell transplantation device of an embodiment.

After the placement step, the withdrawal step of the needles 21 from the target site Sk is performed. The withdrawal step will now be described. First, by the action of the driving part 40, one of the plurality of movable units 10 is moved in a direction away from the surface of the target site Sk. The needles 21 of the movable unit 10 are thereby withdrawn from the target site Sk. The movable unit 10 is moved to a position in which the tip parts of the needles 21 enter a space surrounded by the outer peripheral part 30. FIG. 16 shows a state in which, among the six movable units 10, the movable unit 10*a* located at the far left in the figure is moved to withdraw the needles 21 of the movable unit 10*a* from the target site Sk. The transplants Cg are placed inside the target site Sk.

Figure 17:
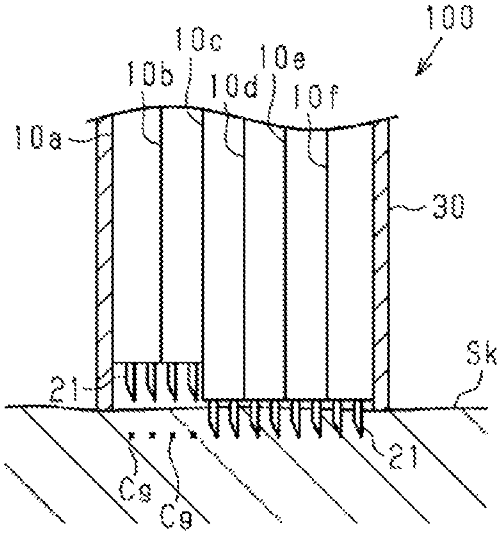
FIG. 17 is a view illustrating a withdrawal step of needles in a transplantation method using a cell transplantation device of an embodiment.
Figure 18:
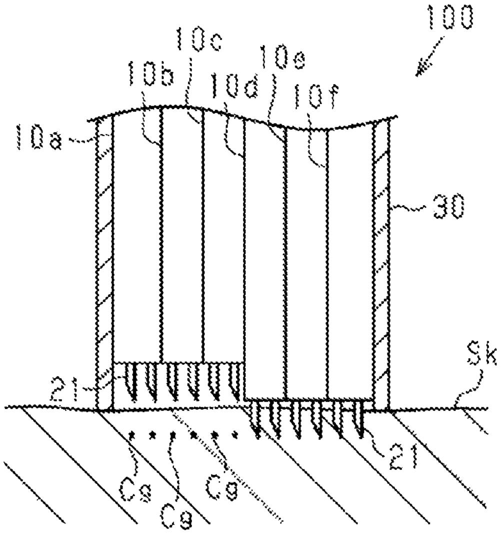
FIG. 18 is a view illustrating a withdrawal step of needles in a transplantation method using a cell transplantation device of an embodiment.
Figure 19:
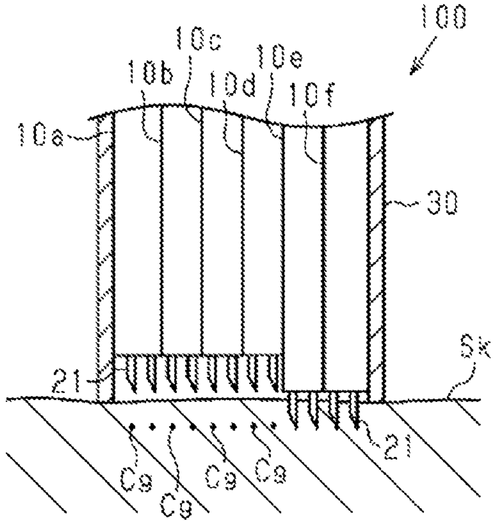
FIG. 19 is a view illustrating a withdrawal step of needles in a transplantation method using a cell transplantation device of an embodiment.
Figure 20:
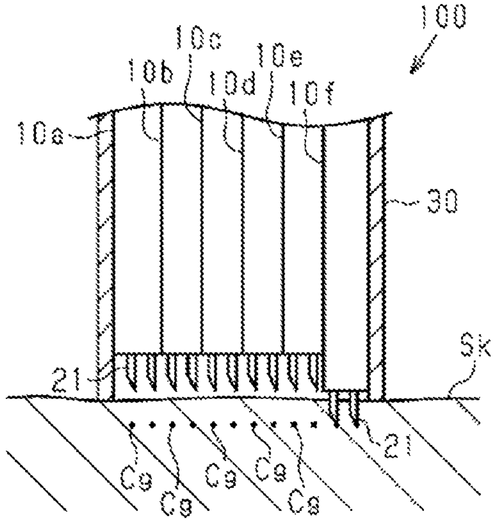
FIG. 20 is a view illustrating a withdrawal step of needles in a transplantation method using a cell transplantation device of an embodiment.
Figure 21:
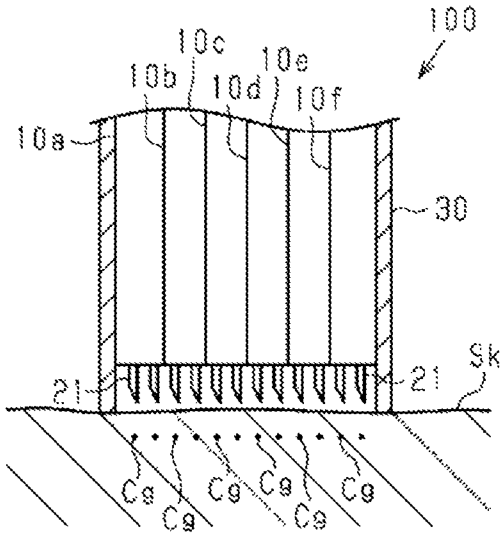
FIG. 21 is a view illustrating a withdrawal step of needles in a transplantation method using a cell transplantation device of an embodiment.

Similarly, the plurality of movable units 10 are moved one by one to sequentially withdraw the needles 21 from the target site Sk for each movable unit 10. For example, the movable units 10 are moved one by one from left to right in the figure. That is, following the movable unit 10*a*, as shown in FIG. 17, the movable unit 10*b* adjacent to the movable unit 10*a* is moved to withdraw the needles 21 of the movable unit 10*b* from the target site Sk. As shown in FIGS. 18, 19, 20, and 21 in sequence, the movable units 10 are moved in the order from the movable unit 10*c*, the movable unit 10*d*, the movable unit 10*e*, and the movable unit 10*f* to withdraw the needles 21 of each movable unit 10 from the target site Sk. As shown in FIG. 21, the last movable unit 10*f* is moved to withdraw the needles 21 of the movable unit 10*f* from the target site Sk, so that all of the needles 21 of the cell transplantation device 100 are withdrawn from the target site Sk. At this time, the tip parts of the needles 21 of all of the movable units 10 do not protrude more than the tip part of the outer peripheral part 30.

Figure 22:
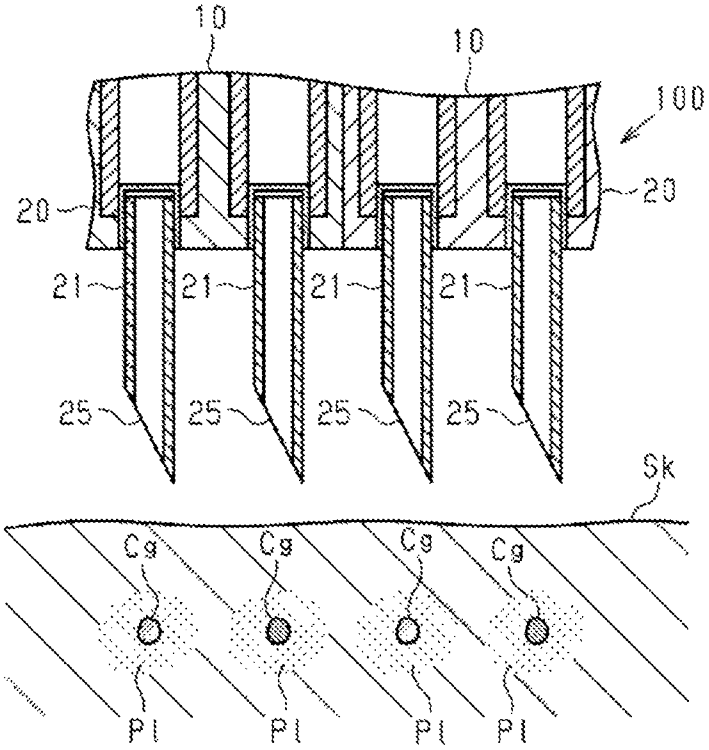
FIG. 22 is a view illustrating a withdrawal step of needles in a transplantation method using a cell transplantation device of an embodiment.

In this manner, as shown in FIG. 22, the transplants Cg remain inside the target site Sk, and the transplantation of the transplants Cg is completed.

Figure 23:
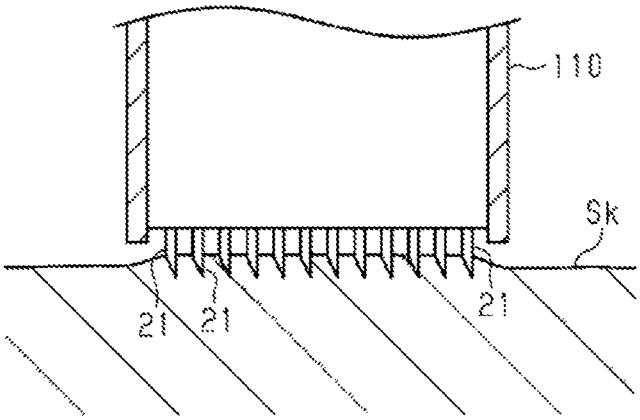
FIG. 23 is a view illustrating a withdrawal step of needles in a transplantation method using a conventional cell transplantation device.

The action of the cell transplantation device 100 of the present embodiment will be described in comparison with the withdrawing step by a conventional cell transplantation device. As shown in FIG. 23, a conventional cell transplantation device 110 does not have movable units that are each independently moved; thus, all needles 21 are withdrawn from the target site Sk at the same time. As a result, the tensile force applied on the target site Sk at one time from the cell transplantation device 110 increases. Since many needles 21 are withdrawn from the target site Sk at close range, the part punctured by each needle 21 receives tensile force due to the withdrawal of other surrounding needles 21 from the surrounding area. As a result, the target site Sk tends to be stretched and pulled up together with the cell transplantation device 110.

When the target site Sk is pulled up after the transplants Cg are placed, the transplants Cg move inside the target site Sk, and the position of the depth of the transplants Cg is likely to deviate from the planned placement depth of the transplants Cg. Since the degree of stretching of the target site Sk varies depending on the puncture position of the needle 21, it is difficult for the conventional cell transplantation device 110 to correct the deviation of the position of depth of the transplants Cg.

In contrast, in the cell transplantation device 100 of the present embodiment, the needles 21 of the plurality of movable units 10 are withdrawn from the target site Sk at different timings. Therefore, compared with the conventional device, the number of needles 21 withdrawn at one time from the target site Sk is reduced. As a result, the tensile force applied on the target site Sk at one time from the cell transplantation device 100 decreases. Further, the tensile force received by the part punctured by each needle 21 from the surrounding area also decreases. For this reason, since the target site Sk is suppressed from being pulled up, the placed transplants Cg are suppressed from moving and their depth from deviating from the planned depth. Furthermore, the deformation of the target site Sk is suppressed, which also suppresses the displacement of the transplants Cg in the direction along the surface of the target site Sk.

Figure 24:
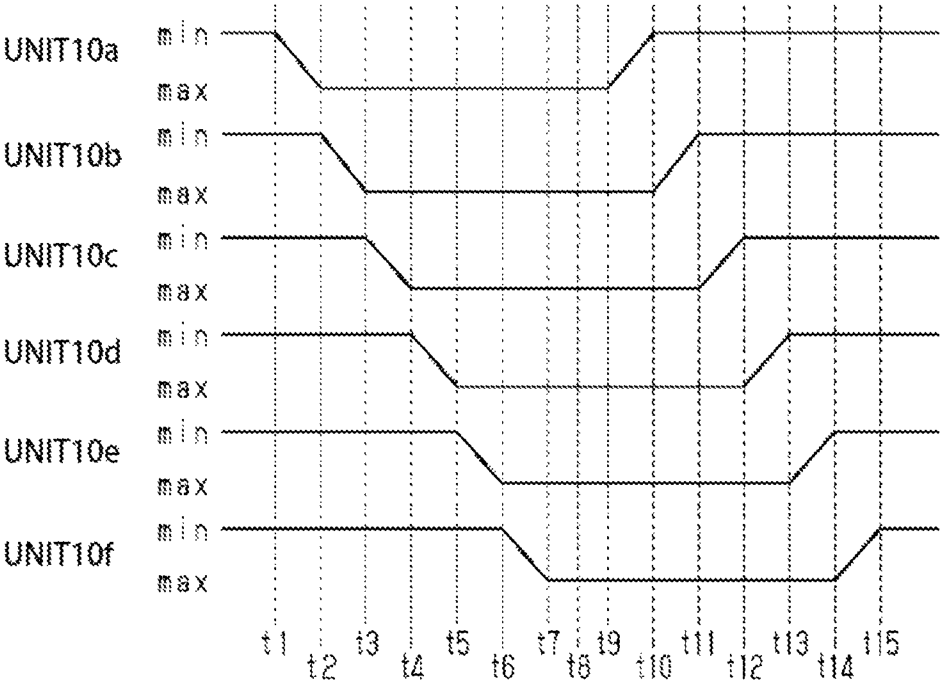
FIG. 24 is a timing chart illustrating changes in the movement of movable units in a cell transplantation device of an embodiment.

FIG. 24 shows an example of the timing of the movement of each movable unit 10 and the release of the transplant Cg. The timing is controlled by the control part 42.

The solid line in FIG. 24 indicates the shift of the position of the tip of the needle 21 in each movable unit 10 in the depth direction of the target site Sk, min indicates a position facing the surface of the target site Sk, and max indicates the deepest puncture position in the target site Sk. When the tip of the needle 21 is located at the position min, the tip part of the needle 21 neither protrudes more than the tip part of the outer peripheral part 30 nor punctures the target site Sk. When the tip of the needle 21 is located at the position max, the tip part of the needle 21 protrudes more than the tip part of the outer peripheral part 30 and punctures the target site Sk. The amount of movement of the movable unit 10 and the length of the needle 21 are set so that the transplant Cg is placed at a desired depth when the needle 21 releases the transplant Cg at the position max.

As shown in FIG. 24, when the cell transplantation device 100 is placed on the target site Sk, the movement of the movable unit 10*a* is started at the timing t1, and the penetration of the needles 21 of the movable unit 10*a* into the target site Sk is started. While the movement of the movable unit 10*a* is stopped at the timing t2 at which the needles 21 of the movable unit 10*a* advance to the position max, the movement of the movable unit 10*b* is started, and the needles 21 of the movable unit 10*b* start penetrating into the target site Sk. Similarly, at the timing at which the needles 21 of the moving movable unit 10 advance to the position max and the movement of the movable unit 10 is stopped, the movement of the adjacent movable unit 10 is started. That is, the movable unit 10*c* at the timing t3, the movable unit 10*d* at the timing t4, the movable unit 10*e* at the timing t5, and the movable unit 10*f* at the timing t6 start moving with the stop of the adjacent movable unit 10.

In this manner, at the timing t7 at which the needles 21 of the movable unit 10*f* advance to the position max, the penetration of the needles 21 of all of the movable units 10 into the target site Sk is completed. Subsequently, the inside of each needle 21 is pressurized at the timing t8 to thereby release the transplant Cg from each needle 21, and place the transplants Cg inside the target site Sk.

Thereafter, the movement of the movable unit 10*a* is started at the timing t9, and the withdrawal of the needles 21 of the movable unit 10*a* from the target site Sk is started. While the movement of the movable unit 10*a* is stopped at the timing t10 at which the needles 21 of the movable unit 10*a* are pulled up to the position min, the movement of the movable unit 10*b* is started, and the withdrawal of the needles 21 of the movable unit 10*b* is started. Similarly, at the timing at which the needles 21 of the moving movable unit 10 are pulled up to the position min and the movement of the movable unit 10 is stopped, the movement of the adjacent movable unit 10 is started. That is, the movable unit 10*c* at the timing t11, the movable unit 10*d* at the timing t12, the movable unit 10*e* at the timing t13, and the movable unit 10*f* at the timing t14 start moving with the stop of the adjacent movable unit 10.

At the timing t15 at which the needles 21 of the movable unit 10*f* are pulled up to the position min, the withdrawal of the needles 21 from the target site Sk is completed for all of the movable units 10, and the transplantation of the transplants Cg is completed.

As described above, at the timing at which the movement of one movable unit 10 is stopped, the movement of the next movable unit 10 is started; thus, the time required for the movement of all of the movable units 10 can be shortened, compared with the case where the movement of the next movable unit 10 is started at intervals after the movement of one movable unit 10 is stopped. Therefore, the transplantation efficiency is increased.

After the penetration step of the needles 21 is completed for all of the movable units 10, the placement step is correctively performed for the needles 21 of all of the movable units 10. After the completion of this step, the withdrawal step of the needles 21 of each movable unit 10 is performed. Therefore, the step executed by the cell transplantation device 100 is always one of the penetration step, placement step, and withdrawal step. Different steps do not occur at the same time; for example, the penetration step of one movable unit 10 and the placement step of another movable unit 10 are not performed at the same time. Accordingly, the operation of the cell transplantation device 100 is suppressed from becoming complicated, and the stability of the implementation of each step is improved. In addition, for example, it is also easy to provide a step of confirming whether these steps are completed properly after the penetration step and the placement step for all of the needles 21.

The timing of the movement of the plurality of movable units 10 is not limited to the above example. The above example shows an embodiment in which the plurality of movable units 10 are moved in the order from the end; however, the order of movement of the movable units 10 is not particularly limited. For example, when the plurality of movable units 10 are arranged in two dimensions, such as concentric circles or lattices, the movable units 10 may be moved in the order from the central portion to the edge of the arrangement, or from the edge to the central portion. Alternatively, the order of movement of the movable units 10 may be random with respect to the arrangement of the movable units 10. Moreover, in the penetration step and the withdrawal step of the needles 21, the order of movement of the movable units 10 may be different.

In each of the penetration step and the withdrawal step, the movement of the next movable unit 10 may be started at intervals after the movement of one movable unit 10 is completed, or the movement of the next movable unit 10 may be started before the movement of one movable unit 10 is completed.

Moreover, all of the movable units 10 may not be moved at different timings. That is, the plurality of movable units 10 may not be moved one by one. If the timing of the movement of some of the plurality of movable units 10 is different from the others, the deviation of the placement depth of the transplants Cg can be suppressed in comparison with a conventional cell transplantation device comprising the same number of needles 21 as in the cell transplantation device 100 of the present embodiment, wherein all of the needles 21 are inserted and withdrawn from the target site Sk at the same time.

When some of the plurality of movable units 10 are moved at the same time, the farther the movable units 10 that are moved at the same time are away from each other, the smaller the tensile force received by the part punctured by each needle 21 from the surrounding area in the target site Sk. Therefore, the deviation of the placement depth of the transplants Cg decreases.

From such a viewpoint, the adjacent movable units 10 are preferably moved at different timings. Further, in the movable units 10 that are moved at the same timing, the distance between the closest needles 21 is preferably 4 mm or more. Alternatively, when the plurality of needles 21 are regularly arranged in the movable units 10, the distance between the closest needles 21 in the movable units 10 that are moved at the same timing is preferably 3 times larger than the arrangement intervals of the needles 21 in the movable units 10.

The cell transplantation device 100 may perform different steps among the penetration step, placement step, and withdrawal step at the same time for the different movable units 10. For example, the penetration step, placement step, and withdrawal step may be continuously performed for each movable unit 10, and the timing of the start of the series of steps may be different for each movable unit 10. That is, the penetration step may be started in sequence for the plurality of movable units 10, the placement step may be performed in the order from the movable unit 10 that has completed the penetration step, and the withdrawal step may be performed in the order from the movable unit 10 that has completed the placement step. According to an embodiment in which the penetration step, placement step, and withdrawal step are continuously performed for each movable unit 10, as shown in FIG. 24 mentioned above, it is possible to reduce the time required to complete the transplantation of all of the transplants Cg, compared with an embodiment in which each step is performed one by one.

As above, according to the above embodiment, the following advantages are obtained.

(1) A plurality of movable units 10 are configured such that each movable unit 10 is movable along the extending direction of the needles 21. Therefore, the timing at which the needle 21 punctures the living organism and the timing at which the needle 21 is withdrawn from the living organism can be different between the plurality of needles 21 provided in the cell transplantation device 100. That is, the timing at which one needle 21 punctures the living organism or is withdrawn from the living organism can be different from the other needles 21. Therefore, compared with the case where all of the needles 21 are inserted or withdrawn from the living organism at the same time, the force received by the target site Sk of transplantation in the living organism at one time from the cell transplantation device 100 decreases, and the force due to the insertion and withdrawal of the needles in the surrounding area received by the part punctured by each needle 21 also decreases. This suppresses expansion and contraction of the target site, so that the placement depth of the transplants Cg is suppressed from deviating from the planned depth.

(2) When the control unit 42 moves the movable units 10 toward the living organism to allow the needle-shaped parts 21 to penetrate the living organism, the movable units 10 adjacent to each other among the plurality of movable units 10 stop moving at different timings. That is, each movable unit 10 stops at a timing different from the stop of the movement of the other adjacent movable unit 10. Therefore, compared with the case where all of the needles 21 puncture the living organism at the same time, the number of needles 21 that puncture the target site Sk at the same time is reduced. As a result, the load received by the target site Sk at one time from the cell transplantation device 100 decreases. Since the moving units 10 adjacent to each other move at different timings, the number of needles 21 that puncture the target site Sk at the same time at close range is reduced. Therefore, the part punctured by each needle-shaped part 21 is subjected to accurately reduced tensile force from its surrounding area. Accordingly, since the target site Sk is suppressed from being stretched and depressed, the puncture depth of the needles 21 is suppressed from deviating from the planned depth; that is, the placement depth of the transplants Cg is suppressed from deviating from the planned depth.

(3) When the control unit 42 moves the movable units 10 in a direction away from the living organism to withdraw the needle-shaped parts 21 from the living organism, the movable units 10 adjacent to each other among the plurality of movable units 10 start moving at different timings. That is, each movable unit 10 starts moving at a timing different from the start of the movement of the other adjacent movable unit 10. Therefore, compared with the case where all of the needles 21 are withdrawn from the living organism at the same time, the number of needles 21 that are withdrawn from the target site Sk at the same time is reduced. As a result, the tensile force received by the target site Sk at one time from the cell transplantation device 100 decreases. Further, since the movable units 10 adjacent to each other move at different timings, the number of needles 21 that are withdrawn from the target site Sk at the same time at close range is reduced. Therefore, the part punctured by each needle-shaped part 21 is subjected to accurately reduced tensile force from its surrounding area. Accordingly, since the target site Sk is suppressed from being stretched and pulled up, the transplants Cg placed inside the target site Sk are suppressed from moving and their depth from deviating from the planned depth.

(4) When the control part 42 moves the movable units 10 toward the living organism to allow the needles 21 to penetrate the living organism, each movable unit 10 stops moving at a timing different from the other movable units 10. That is, each movable unit 10 stops at a timing different from the stop of the movement of the other movable units 10. Since the plurality of movable units 10 are moved one by one, the number of needles 21 that puncture the target site Sk at the same time is further reduced. As a result, the load received by the target site Sk at one time from the cell transplantation device 100 decreases, and the tensile force received by the part punctured by each needle 21 from its surrounding area also decreases. Accordingly, since the target site Sk is further suppressed from being stretched and depressed, the deviation of the puncture depth of the needles 21 is further suppressed; that is, the deviation of the placement depth of the transplants Cg is further suppressed.

(5) When the control part 42 moves the movable units 10 to withdraw the needles 21 from the living organism, each movable unit 10 starts moving at a timing different from the other movable units 10. That is, each movable unit 10 starts moving at a timing different from the start of the movement of the other movable units 10. Since the plurality of movable units 10 are moved one by one, the number of needles 21 that are withdrawn from the target site Sk at the same time is further reduced. As a result, the tensile force received by the target site Sk at one time from the cell transplantation device 100 decreases, and the tensile force received by the part punctured by each needle 21 from its surrounding area also decreases. Accordingly, since the target site Sk is further suppressed from being stretched and pulled up, the deviation of the placement depth of the transplants Cg is further suppressed.

(6) The control part 42 controls the timing of suction by the suction pressure part 41, so that after the penetration of the needles 21 of all of the movable units 10 into the living organism is completed, the transplant Cg is released from each needle 21. Therefore, the mixing of different steps at the same time is suppressed in the cell transplantation device 100. Accordingly, the operation of the cell transplantation device 100 is suppressed from becoming complicated, and the stability of the implementation of each step is improved.

(7) The control part 42 controls the driving part 40 and the suction pressure part 41 to thereby continuously perform penetration of the needles 21 into the living organism, release of the transplants Cg from the needles 21, and withdrawal of the needles 21 from the living organism, for each movable unit 10. Accordingly, compared with the case where the cell transplantation device 100 performs one step at a time, the time required for the completion of the transplantation of all of the transplants Cg can be shortened.

(8) The sum of the needles 21 provided in the plurality of movable units 10 is 5 or more, and the needles 21 are arranged at a density of 5 or more per $cm^2$ in the cell transplantation device 100. Since a plurality of needles 21 are arranged close to each other, it is easy to achieve the above advantages by dividing the needles 21 into a plurality of movable units 10, and controlling the insertion and withdrawal of the needles 21 into and from the living organism at different timings.

(9) When the transplant Cg is a cell aggregate containing skin-derived stem cells, the placement depth of the cell group is suppressed from deviating from the planned depth during transplantation of the cell group into a skin region. The skin region is formed from a plurality of layers, and the placement depth of the cell group and the exertion of the function of the cell group are closely related to each other. Therefore, due to the use of the cell transplantation device 100 for the transplantation of cell groups into the skin region, the effects of transplantation of the cell groups, such as tissue regeneration, are more likely to be precisely achieved. When the transplantation of cell groups is intended for hair growth or hair restoration, it is often required to transplant a large amount of the aforementioned cell groups. Due to the use of the cell transplantation device 100 for transplantation of such cell groups, the cell transplantation efficiency can be greatly increased, and the effects of hair growth and hair restoration can be preferably obtained by the exertion of the function of the cell groups.

[Modification]

The above embodiment can be performed with the following modifications.

- The timing of the movement of the plurality of movable units 10 may be different in at least one of the penetration step and the withdrawal step. That is, in either of the penetration step and the withdrawal step, the needles 21 provided in the cell transplantation device 100 may be moved at the same time with respect to the target site. When the timing of the movement of the plurality of movable units 10 is different in at least one of the penetration step and the withdrawal step, the deviation of the placement depth of the transplants Cg can be suppressed, compared with a conventional cell transplantation device in which all of the needles 21 are inserted and withdrawn at the same time in both the penetration step and the withdrawal step.
- In the plurality of movable units 10, the amount of movement of the movable units 10 and the length of the needles 21 may not be constant. For example, when the distance from the initial position of the needles 21 to the planned placement depth of the transplants Cg is not constant in the plurality of needles 21 because the surface of the target site is curved like a scalp, the amount of movement of some of the movable units 10 may be different from the others, so that each needle 21 penetrates to the planned placement depth of the transplants Cg. Furthermore, the planned placement depth of the transplants Cg, that is, the planned puncture depth of the needles 21, may not be constant in the plurality of needles 21.
- The outer peripheral part 30 may not surround the entire outer periphery of the plurality of movable units 10. The outer peripheral part 30 may be configured, for example, to be able to define the reference position for the movement of the movable units 10 by being brought into contact with the target site.
- The cell group to be transplanted may not be necessarily a cell group that contributes to hair growth or hair restoration, and may be any cell group that exhibits desired effects when placed in a living organism. For example, the cell group to be transplanted may be a cell group that exhibits effects in cosmetic use such as elimination of wrinkles or improvement in moisturizing state in the skin. Furthermore, the object transferred by the transfer device for a living organism into the living organism is not limited to a cell group, and may be solids such as drugs.

What is claimed is:

1. A transfer device for a living organism for placing an object into the living organism, comprising:

a plurality of movable units, each movable unit of the plurality of movable units comprising at least two identical needles extending in a first direction, each needle having a cylindrical shape storing the object therein, each movable unit of the plurality of movable units being configured to move in the first direction, a control part that independently controls movement of each of the plurality of movable units in the first direction, and a suction pressure part applying suction to an inside space of each of the two or more identical needle to incorporate the object into the respective needle and pressurizing the inside space of the respective needle to release the object from the respective needle, wherein the control part is configured to consequently move each of the plurality of movable units towards the living organism so that each of the needles of each of the plurality of movable units penetrate the living organism for the same penetration depth, the control part is further configured to release the object into the living organism after the needles of each of the plurality of movable units penetrate the living organism for the same penetration depth, the control part is configured to initiate first movement of a first unit of the plurality of movable units and then for each subsequent unit of the plurality of movable units, the control part is configured to initiate movement of a respective unit at a time when the movement of a preceding adjacent unit stops after penetrating to said penetrating depth;

the control part is configured to consequently withdraw each of the plurality of movable units from the living organism; the control part is configured to initiate first movement of a unit of the plurality of movable units to withdraw the unit from the living organism and then for each subsequent unit of the plurality of movable units, the control part is configured to initiate withdrawal movement of the respective unit to withdraw the respective unit from the living organism at a time when a preceding adjacent unit of the plurality of movable units completes withdrawal movement from the living organism, wherein the object consists of a liquid and a cell aggregate, and each of the at least two identical needles comprises (a) a first tube including a tip part of the needle, (b) a second tube including a base end of the needle, the second tube having a larger flow passage cross-sectional area than that of the first tube, and (c) a stopper at a junction between the first tube and the second tube, an internal space of the first tube and the internal space of the second tube communicate with each other and form a single flow passage of the needle, the stopper crosses the flow passage of the needle in a middle of the flow passage, the stopper allows passing of the liquid material of the object from the tip part of the respective needle to the base end of the respective needle with respect to the stopper, while preventing passing of the cell aggregate of the object from the tip part of the respective needle to the base end of the respective needle with respect to the stopper.

2. The transfer device of claim 1, wherein the control part is configured to move each movable unit of the plurality of movable units to continuously perform the penetration of the needles into the living organism, the release of the object accommodated in the needles from the needles, and the withdrawal of the needles from the living organism.

3. The transfer device of claim 1, wherein a sum of the needles provided in the plurality of movable units is 5 or more, and the needles are arranged at a density of 5 or more per $cm^2$.

4. The transfer device of claim 1, wherein the object is a cell aggregate containing skin-derived stem cells.

5. The transfer device of claim 1, wherein the plurality of movable units are arranged in a two-dimensional square or hexagonal lattice shape.

6. The transfer device of claim 1, wherein the plurality of movable units are arranged linearly.

7. The transfer device of claim 1, wherein each movable unit of the plurality of movable units comprises two or more and ten or less identical needles extending in the first direction.

8. The transfer device of claim 1, wherein the plurality of movable units comprise at least six movable units.

9. The transfer device of claim 1, wherein the at least two needles are the only objects extending from each movable unit of the plurality of movable units in the first direction.

10. The transfer device of claim 1, wherein further comprising a drive unit moving each movable unit of the plurality of movable units along the first direction.

11. The transfer device of claim 10, further comprising an outer peripheral part surrounding the plurality of movable units, wherein the drive unit moves each movable unit of the plurality of movable units between a first position in which tip parts of the at least two identical needles do not protrude more than a tip part of the outer peripheral part, and a position in which the tip parts of the at least two identical needles protrude more than the tip part of the outer peripheral part in the first direction.

12. The transfer device of claim 10, wherein the drive unit includes an electrical a motor, and moves each movable unit of the plurality of movable units independently depending on a control signal from the control part.

13. The transfer device of claim 1, wherein each movable unit of the plurality of movable units further comprises a support part supporting the at least two identical needles.

14. The transfer device of claim 1, wherein the tip part of each of the at least two identical needles is truncated obliquely relative to the first direction.

15. The transfer device of claim 1, wherein the suction pressure part performs said applying and said pressurizing in response to a control signal from the control part.

16. The transfer device of claim 1, wherein the suction pressure part performs said applying and said pressurizing separately for each movable unit of said plurality of movable units.

17. The transfer device of claim 1, wherein the suction pressure part performs said applying and said pressurizing collectively for plurality of movable units.

* * * * *